US010308681B2

(12) United States Patent
Choung et al.

(10) Patent No.: US 10,308,681 B2
(45) Date of Patent: *Jun. 4, 2019

(54) PHARMACEUTICAL COMPOSITION FOR THE PREVENTION AND TREATMENT OF CARDIOVASCULAR DISEASE COMPRISING THE PEPTIDE HAVING THE ABILITY TO INHIBIT ANGIOTENSIN-1 CONVERTING ENZYME AS AN ACTIVE INGREDIENT

(71) Applicants: University-Industry Cooperation Group of Kyung Hee University, Yongin-si, Gyeonggi-do (KR); Industry-Academic Cooperation Foundation Gyeongsang National University, Jinju-si, Gyeongsangnam-do (KR)

(72) Inventors: Se-Young Choung, Seoul (KR); Yeung Joon Choi, Tongyeong-si (KR)

(73) Assignees: UNIVERSITY-INDUSTRY COOPERATION GROUP OF KYUNG HEE UNIVERSITY, Yongin-si, Gyeonggi-Do (KR); INDUSTRY-ACADEMIC COOPERATION FOUNDATION GYEONGSANG NATIONAL UNIVERSITY, Jingu-si, Gyeongsangnam-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/856,926

(22) Filed: Dec. 28, 2017

(65) Prior Publication Data

US 2018/0170961 A1    Jun. 21, 2018

Related U.S. Application Data

(60) Division of application No. 14/627,642, filed on Feb. 20, 2015, which is a continuation-in-part of application No. PCT/KR2013/007598, filed on Aug. 23, 2013.

(30) Foreign Application Priority Data

Aug. 24, 2012  (KR) .................. 10-2012-0092738
Aug. 23, 2013  (KR) .................. 10-2013-0100232

(51) Int. Cl.
| C07K 5/062 | (2006.01) |
| C07K 5/078 | (2006.01) |
| C07K 5/068 | (2006.01) |
| C07K 5/083 | (2006.01) |
| C07K 5/097 | (2006.01) |
| C07K 5/087 | (2006.01) |
| C07K 5/065 | (2006.01) |

(52) U.S. Cl.
CPC ........ *C07K 5/06086* (2013.01); *C07K 5/0606* (2013.01); *C07K 5/06026* (2013.01); *C07K 5/06034* (2013.01); *C07K 5/06052* (2013.01); *C07K 5/06069* (2013.01); *C07K 5/06078* (2013.01); *C07K 5/06165* (2013.01); *C07K 5/0806* (2013.01); *C07K 5/0812* (2013.01); *C07K 5/0823* (2013.01)

(58) Field of Classification Search
CPC ............ C07K 5/06086; C07K 5/06052; C07K 5/0606; C07K 5/06069; C07K 5/06078; C07K 5/06165; C07K 5/0806; C07K 5/0812; C07K 5/0823
See application file for complete search history.

(56) References Cited

U.S. PATENT DOCUMENTS

| 5,972,894 A * | 10/1999 | Sinackevich ......... A61K 38/05 514/17.8 |
| 7,034,002 B1 | 4/2006 | Fujita |
| 2010/0035822 A1 | 2/2010 | Camargo et al. |

FOREIGN PATENT DOCUMENTS

| EP | 2161029 A1 * | 3/2010 |
| JP | 06-279314 | 10/1994 |
| JP | 2012046450 | * 3/2012 |

OTHER PUBLICATIONS

Van Platernick et al., Anal Bioanal Chem (2008) 391:299-307 (Year: 2008).*
Liu et al., Fenxi Kexue Xuebao, Feb. 2012, 28(1), 16-22, with English language STN Abstract (Year: 2012).*
(Continued)

*Primary Examiner* — Karlheinz R. Skowronek
*Assistant Examiner* — Joseph Fischer
(74) *Attorney, Agent, or Firm* — Lucas & Mercanti, LLP

(57) ABSTRACT

The present invention relates to a peptide separated from the fraction of oyster enzyme hydrolysate displaying the ability of suppressing angiotensin converting enzyme (ACE) and a pharmaceutical composition for the prevention and treatment of cardiovascular disease comprising the said peptide as an active ingredient. Particularly, the peptide separated from the fraction of the oyster enzyme hydrolysate of the present invention significantly inhibits ACE activity, and thus brings blood pressure regulating effect and antihypertensive effect. Therefore, the fraction of the oyster enzyme hydrolysate of the invention or the peptide separated from the same can be effectively used as an active ingredient of a pharmaceutical composition for the prevention or treatment of cardiovascular disease.

3 Claims, 8 Drawing Sheets

Specification includes a Sequence Listing.

(56) References Cited

OTHER PUBLICATIONS

Chibuike C. Udenigwe and Rotimi E. Aluko, Food Protein-Derived Bioactive Peptides: Production, Processing, and Potential Health Benefits, Journal of Food Science, 2012, vol. 77, No. 1, pp. R11-R24.
Rajeev Kumar, Arun Kumar, Ramji Sharma, Atul Baruwal, Pharmacological review on Natural ACE inhibitors, Der Pharmacia Lettre, 2010, 2(2): 273-293.
Jae-Young Je, et. al., Isolation of angiotensin I converting enzyme (ACE) inhibitor from fermented oyster sauce, *Crassostrea gigas*, Food Chemistry 90 (2005) 809-814.
Seigo Ono, et. al., Inhibition properties of dipeptides from salmon muscle hydrolysate on angiotensin I-converting enzyme, International Journal of Food Science and Technology 2006, 41, 383-386.
Machine translation of JP 06279314 A, inventors Yoshikawa et al., Assignee Nippon Synthetic Chem Ind, published Oct. 4, 1994 (including STN bibiographic citation).
Tardif et al., Effects of the P-Selectin Antagonist Inclacumab on Myocardial Damage After Percutaneous Coronary Intervention for Non-ST-Segment Elevation Myocardial Infarction Results of the Select-ACS Trial, J Am Coll Card, 61 (20):2048-2055 (2013).
Kegg Drug: Inclacumab entry D10356 including sequence, downloaded Mar. 30, 2017, one page.
International Search Report, PCT/KR2013/007598, dated Nov. 19, 2013.

\* cited by examiner

[FIG. 1]
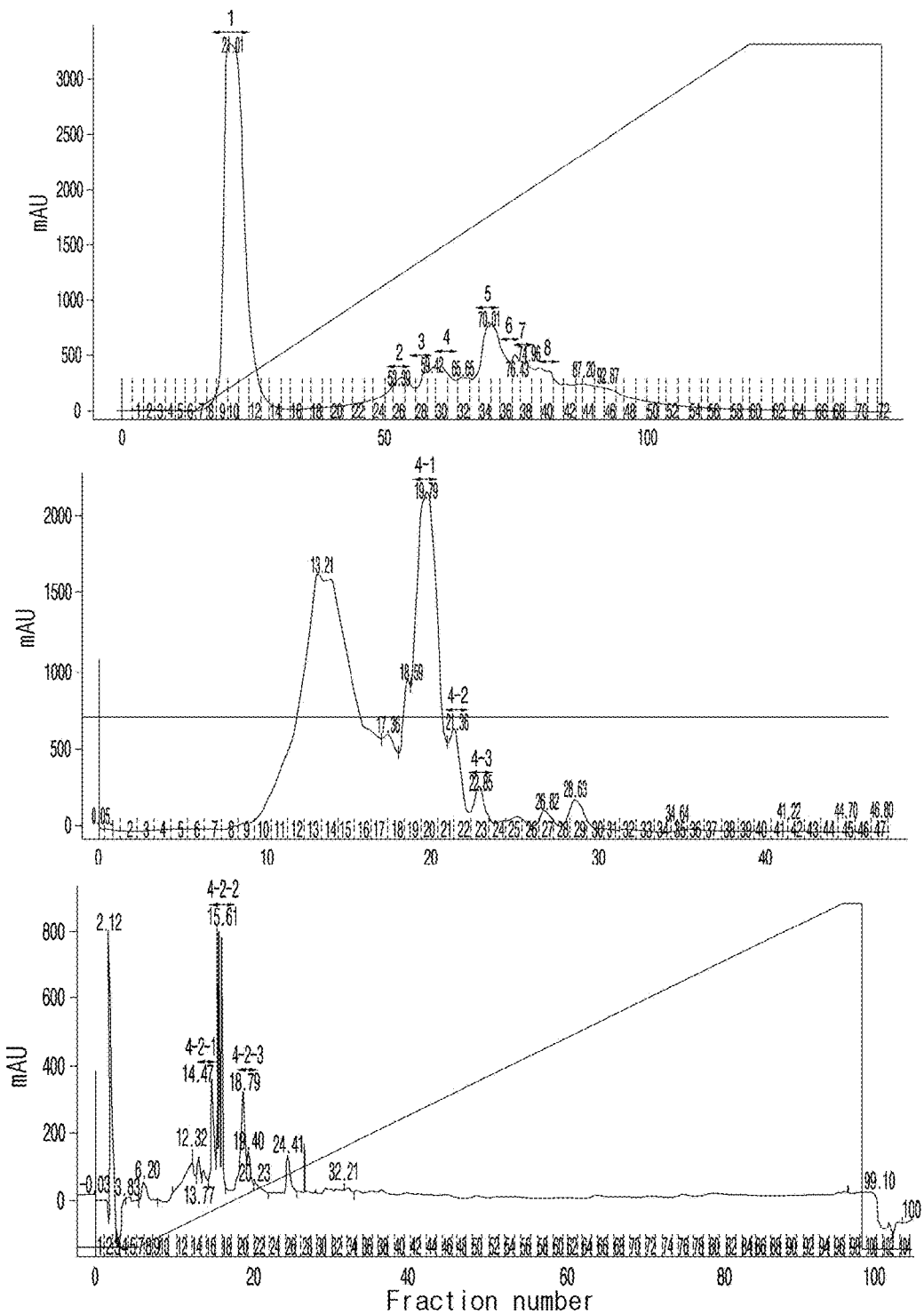

[FIG. 2]
1st and 2nd residue of purified peptide from RP-HPLC
Suggested peptide : KY, TAY
Identification of molecular weight from purified peptide from RP-HPLC
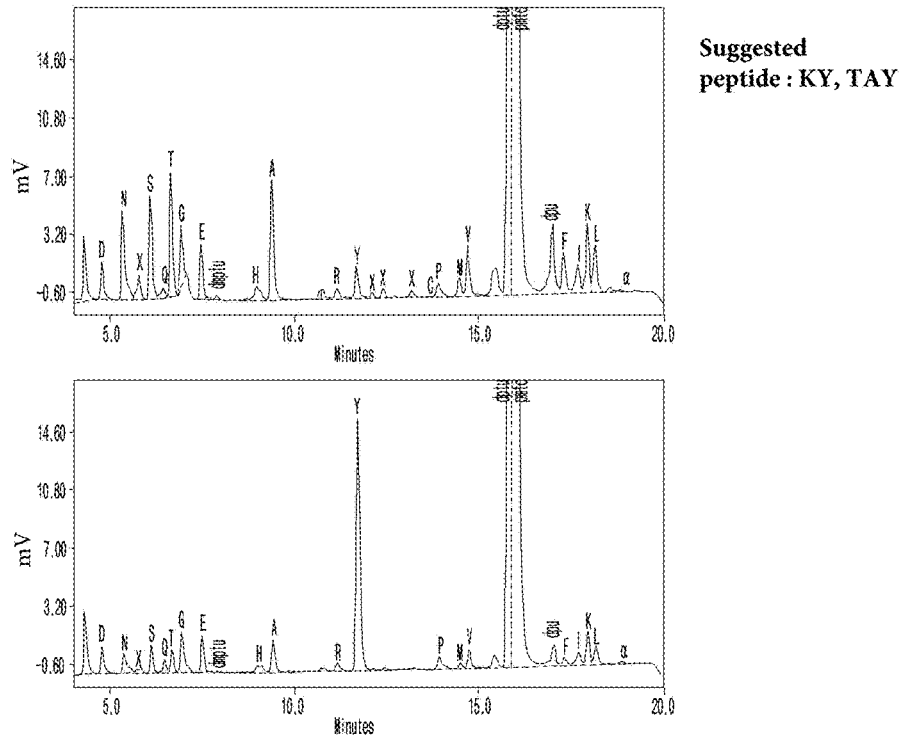
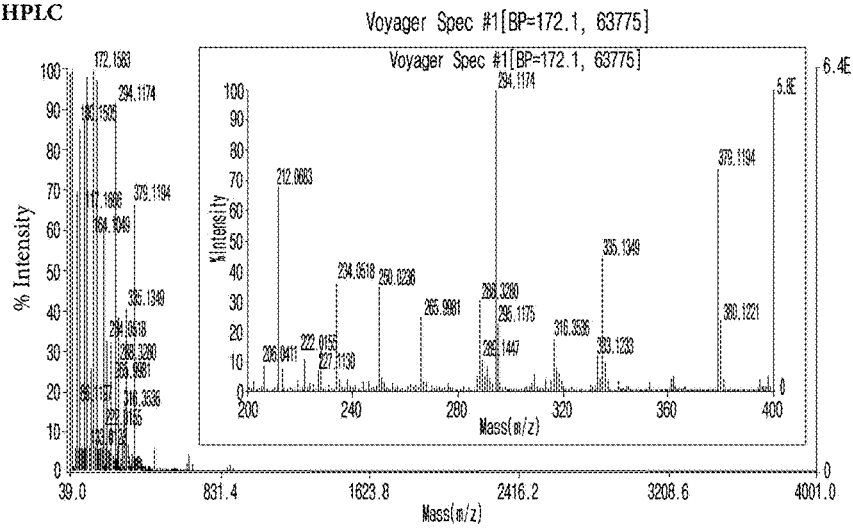

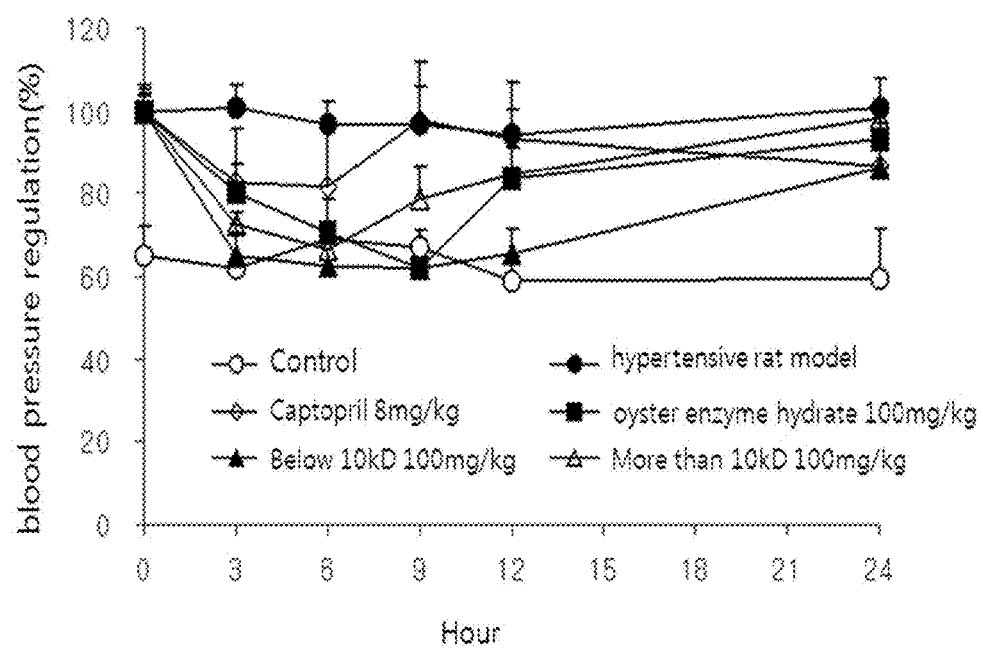
[FIG. 3]

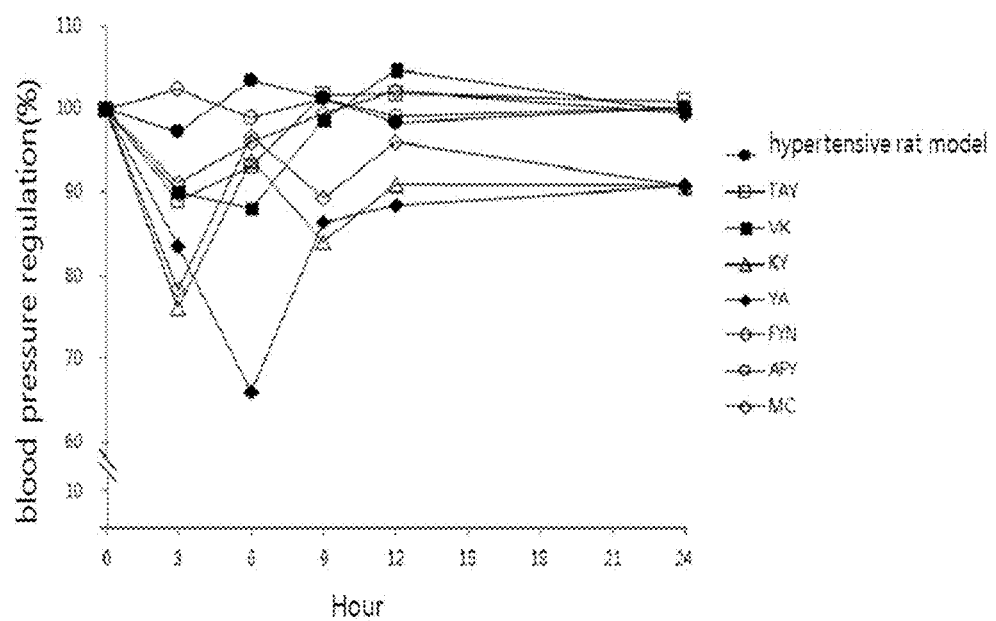
[FIG. 4]

[FIG. 5]
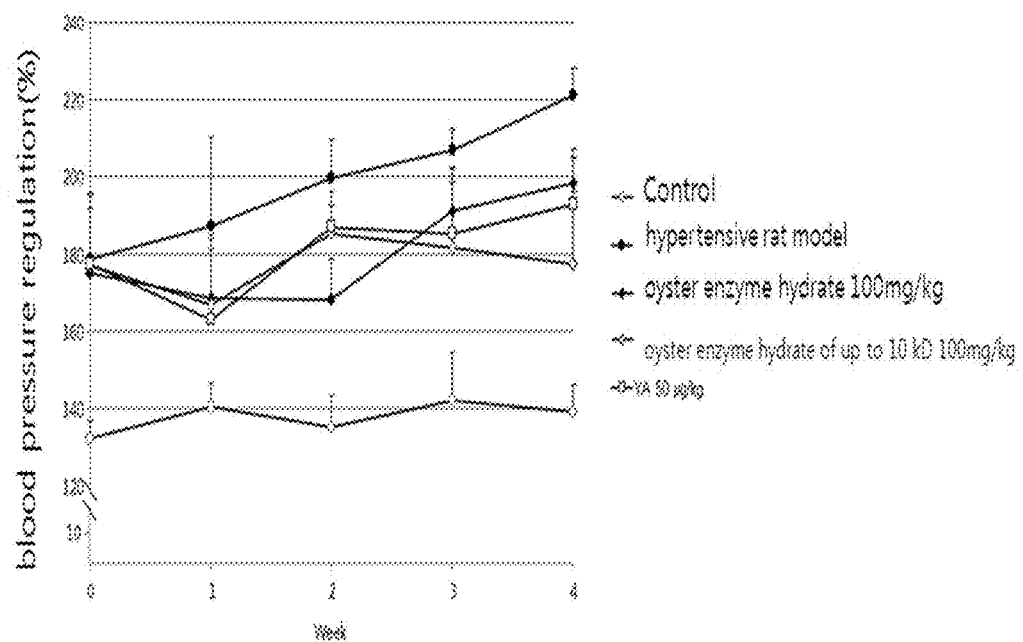

[FIG. 6]
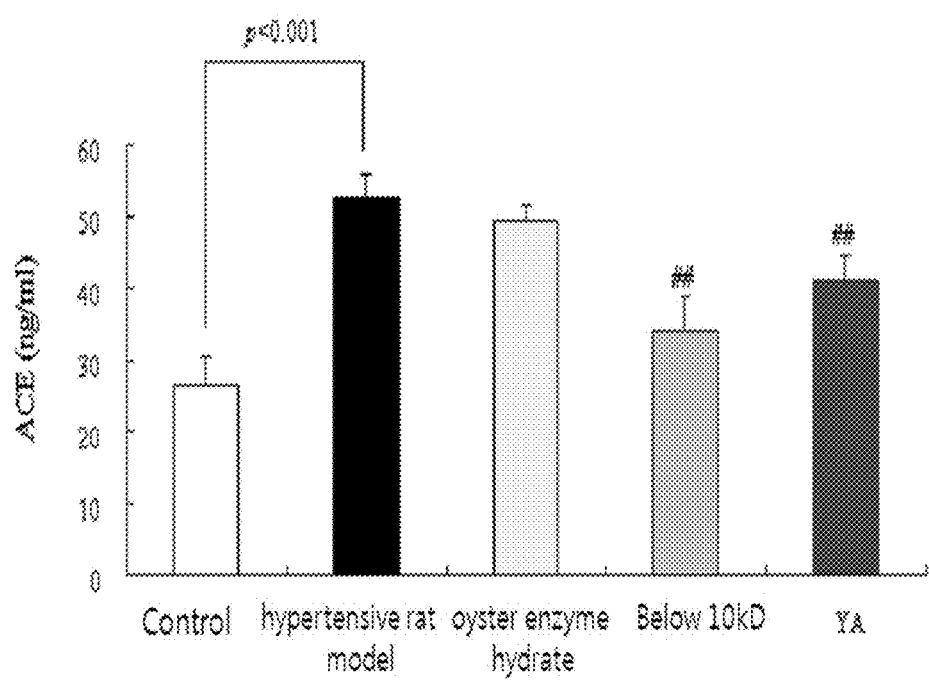

[FIG. 7]
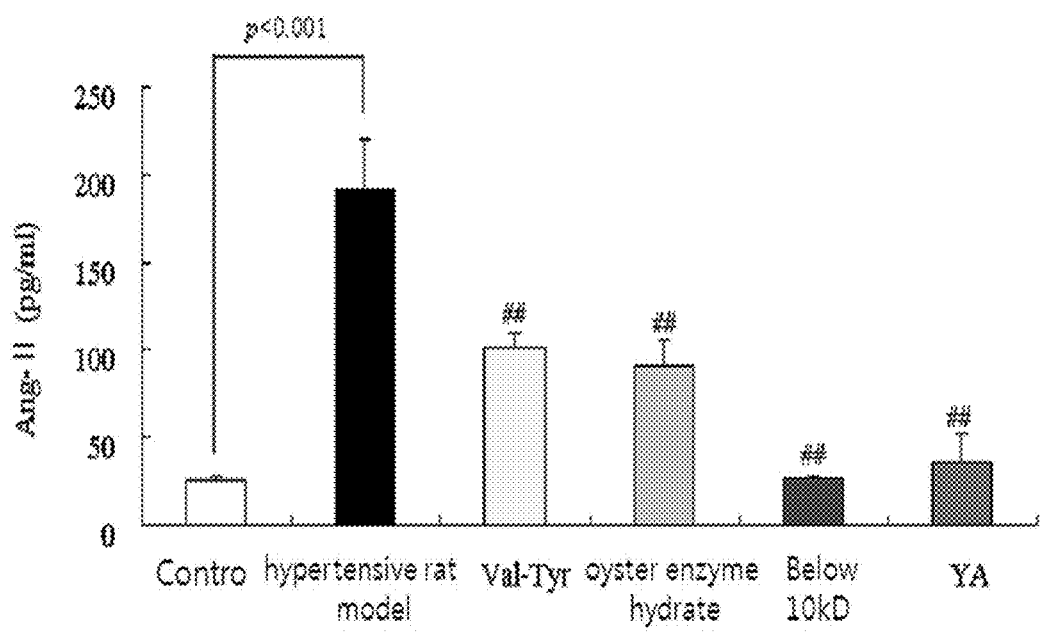

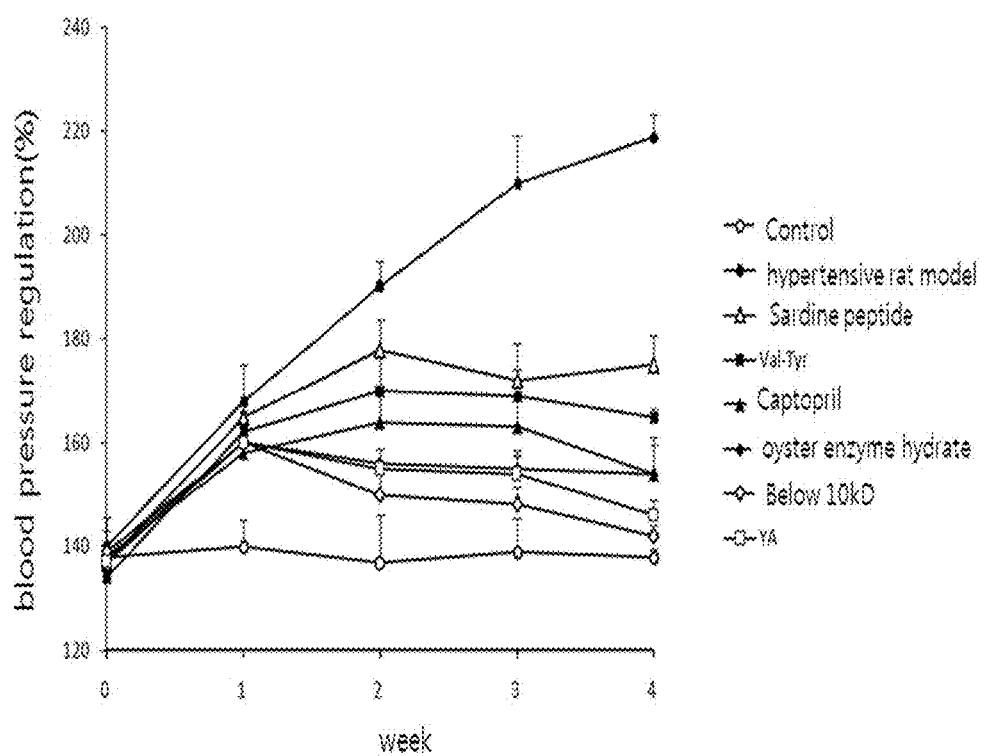
[FIG. 8]

SEQUENCE LISTING

<160> NUMBER OF SEQ ID NOS: 12

<210> SEQ ID NO 1
<211> LENGTH: 3
<212> TYPE: PRT
<213> ORGANISM: oyster

<400> SEQUENCE: 1

Thr Ala Tyr
1

<210> SEQ ID NO 2
<211> LENGTH: 2
<212> TYPE: PRT
<213> ORGANISM: oyster

```
<400> SEQUENCE: 2

Val Lys
  1

<210> SEQ ID NO 3
<211> LENGTH: 2
<212> TYPE: PRT
<213> ORGANISM: oyster

<400> SEQUENCE: 3

Lys Tyr
  1

<210> SEQ ID NO 4
<211> LENGTH: 2
<212> TYPE: PRT
<213> ORGANISM: oyster

<400> SEQUENCE: 4

Tyr Ala
  1

<210> SEQ ID NO 5
<211> LENGTH: 3
<212> TYPE: PRT
<213> ORGANISM: oyster

<400> SEQUENCE: 5

Phe Tyr Asn
  1

<210> SEQ ID NO 6
<211> LENGTH: 3
<212> TYPE: PRT
<213> ORGANISM: oyster

<400> SEQUENCE: 6

Ala Phe Tyr
  1

<210> SEQ ID NO 7
<211> LENGTH: 2
<212> TYPE: PRT
<213> ORGANISM: oyster

<400> SEQUENCE: 7

Met Cys
  1

<210> SEQ ID NO 8
<211> LENGTH: 3
<212> TYPE: PRT
<213> ORGANISM: oyster

<400> SEQUENCE: 8

Gly Pro Asn
  1

<210> SEQ ID NO 9
<211> LENGTH: 3
<212> TYPE: PRT
<213> ORGANISM: oyster

<400> SEQUENCE: 9
```

```
Ala Phe Asn
  1

<210> SEQ ID NO 10
<211> LENGTH: 3
<212> TYPE: PRT
<213> ORGANISM: oyster

<400> SEQUENCE: 10

Pro Gly Asn
  1

<210> SEQ ID NO 11
<211> LENGTH: 2
<212> TYPE: PRT
<213> ORGANISM: oyster

<400> SEQUENCE: 11

Pro His
  1

<210> SEQ ID NO 12
<211> LENGTH: 2
<212> TYPE: PRT
<213> ORGANISM: oyster

<400> SEQUENCE: 12

Ser Phe
  1
```

PHARMACEUTICAL COMPOSITION FOR THE PREVENTION AND TREATMENT OF CARDIOVASCULAR DISEASE COMPRISING THE PEPTIDE HAVING THE ABILITY TO INHIBIT ANGIOTENSIN-1 CONVERTING ENZYME AS AN ACTIVE INGREDIENT

CROSS REFERENCE TO RELATED APPLICATIONS

This application is a divisional of U.S. patent application Ser. No. 14/627,642 filed Feb. 20, 2015, which is a continuation-in-part of PCT/KR2013/007598 filed Aug. 23, 2013 which claims the benefit of Korean patent applications KR-10-2012-0092738 filed Aug. 24, 2012 and KR-10-2013-0100232 filed Aug. 23, 2013, the contents of each of which are incorporated herein by reference in their entirety.

BACKGROUND OF THE INVENTION

1. Field of the Invention

The present invention relates to a peptide separated from the fraction of the oyster enzyme hydrolysate displaying the ability of suppressing angiotensin converting enzyme (ACE) and a pharmaceutical composition for the prevention and treatment of cardiovascular disease comprising the said peptide as an active ingredient.

2. Description of the Related Art

According to the rapid economic development, the pattern and the aspect of disease have also been changed, so that cardiovascular disease is remarkably increasing, for example arteriosclerosis, hypertension, angina pectoris, myocardial infarction, ischemic heart disease, heart failure, complications caused by transluminal coronary angioplasty, cerebral infarction, cerebral hemorrhage, and stroke are in increase. According to the ranking of cause of death reported by Statistics Korea in 2010, cardiovascular disease is ranked as the second topmost cause of death in Korea, which is next to malignant tumor. Particularly, death rate of cardiovascular disease is significantly increased in male over 55 years of age and in female over 65 years of age.

The most representative cardiovascular disease, hypertension, takes 15~20% of total adult disease, making it a world-wide health issue. Even though there is no specific symptoms in hypertension patients, it is highly required to control and treat the disease because the risk of the same complications as shown in other cardiovascular diseases such as arteriosclerosis, stroke, myocardial infarction and end-stage renal disease is still high. Hypertension is a chronic disease that requires life-long treatment, suggesting that social and economical loss is great.

The cause of hypertension is still unknown, but is presumed to be developed by genetic factors such as family history, races, salt intake, insulin resistance, and obesity and/or environmental factors such as excessive drinking and aging, etc. Among many factors that are involved in raising blood pressure, renin-angiotensin-aldosterone cycle has been known to play an important role in regulating blood pressure and body fluid level in vivo (Weiss, D. et. al (2001) Circulation 103: 448-454).

In particular, renin-angiotensin system (RAS) has been known to play an important role in the development of essential hypertension which takes 80% of total hypertension cases. In general, renin-angiotensin system is activated when the blood flow rate or sodium level is dropped in the kidney or when the activity of sympathetic nervous system is increased. Renin secreted in juxtaglomerular cells in renal artery decomposes angiotensin into angiotensin I and then angiotensin I is converted into angiotensin II inducing the contraction of blood vessel by angiotensin converting enzyme (ACE). As a result, angiotensin II regulates blood pressure by increasing aldosterone synthesis and by neuro-regulation. ACE also decomposes bradykinin having vasodilating activity so as to inactivate bradykinin.

Therefore, angiotensin converting enzyme inhibitor (ACE inhibitor) is expected to be able to treat or prevent cardiovascular diseases such as hypertension, heart disease, arteriosclerosis, or cerebral hemorrhage, considering that ACE has a great effect on blood pressure increase, on which therefore studies have been focused. Particularly, various clinical attempts have been made to confirm if the decrease of the cases and even the death rate of chronic kidney disease, arteriosclerosis, and heart attack could be achieved by such ACE inhibitor and the results thereby have been reported.

Based on the above reports, chemically synthesized angiotensin converting enzyme inhibitors such as ramipril, captopril, enarapil, risinopril, fosinoril, and spirapril are commercialized and used as hypertension treating agents. However, these compounds are so easily decomposed in a pharmaceutical administration form, that means stability is low, and they cause side effects by affecting other cells including weakness of whole body, vomiting, cough, headache, anorexia, and taste disorder, etc. (Lim S D. et. al (2008) Korean J. Food Sci. Ani. Resour, 28(5): 587-595). Thus, it is required to develop a natural ACE inhibitor that has increased stability but has less side effects in vivo.

Oyster, nicknamed "the milk from the ocean," has been known as an excellent health food. Even in Western countries, where live sea food is not eaten as often as in Asian countries, live oyster is eaten. As nutrition factors, oyster contains glycogen, taurine, protein, vitamin, and various minerals, making an excellent substance for health food. Oyster is also effective in strengthening the functions of heart and liver, in treating hypertension and arteriosclerosis, and in preventing heart disease. Since oyster contains a plenty of selenium, it not only has detoxication activity for heavy metals but also is known as the tonic and stamina food increasing the functions of heart, liver, pancreas, and other organs.

As for the known natural ACE inhibitors so far, Korean Patent Publication No. 10-2012-0092735 describes the composition for inhibiting angiotensin converting enzyme, or having antihypertensive or antidiabetic property, comprising *Capsosiphon fulvescens* extract treated by enzyme. Korean Patent No. 10-1275766 describes the composition for inhibiting angiotensin converting enzyme, or having antihypertensive or antiobese property, comprising protein extract of abalone intestine The peptides having ACE inhibiting activity have been identified from the enzyme hydrolysates of natural substances. Among them, valine-tyrosine, the peptide originated from sardine protein has been confirmed to have the activity of reducing blood pressure in mild hypertension patients (Shimizu, M (1994) Melbourne September, 18), because of which it has been approved as the first individual case-authorized health food in Korea. Korean Patent No. 10-1106303 describes the ACE inhibiting activity of the peptide prepared from oyster. However, the need for the development of natural substance derived functional peptides is still in increase.

Therefore, the present inventors tried to identify a peptide having ACE inhibiting activity from the enzyme hydrolysates of natural substances. As a result, the present inventors obtained a novel peptide having ACE inhibiting activity by extracting, separating, and purifying the peptide from oyster enzyme hydrolysates. Thereafter, the present inventors completed this invention by confirming that the novel peptide identified by the inventors had the effect of regulating blood pressure and of preventing hypertension thereby so that the peptide separated from oyster enzyme hydrolysates could be effectively used as an active ingredient of a pharmaceutical composition for the prevention or treatment of cardiovascular disease.

SUMMARY OF THE INVENTION

It is an object of the present invention to provide a peptide having angiotensin converting enzyme (ACE) inhibiting activity comprising one of the amino acid sequences represented by SEQ. ID. NO: 1~NO: 12.

It is another object of the present invention to provide a pharmaceutical composition for the prevention and treatment of cardiovascular disease comprising the fraction of the oyster enzyme hydrolysate containing the said peptide as an active ingredient.

It is also an object of the present invention to provide a pharmaceutical composition for the prevention or treatment of cardiovascular disease comprising at least one of the said peptides as an active ingredient.

It is further an object of the present invention to provide a health food for the prevention or improvement of cardiovascular disease comprising the fraction of the oyster enzyme hydrolysate containing the said peptide as an active ingredient.

It is also an object of the present invention to provide a health food for the prevention or improvement of cardiovascular disease comprising at least one of the said peptides as an active ingredient.

It is also an object of the present invention to provide a method for treating cardiovascular disease containing the step of administering the fraction of the oyster enzyme hydrolysate comprising the said peptide to a subject having cardiovascular disease.

It is also an object of the present invention to provide a method for treating cardiovascular disease containing the step of administering at least one of the said peptides to a subject having cardiovascular disease.

It is also an object of the present invention to provide a method for preventing cardiovascular disease containing the step of administering the fraction of the oyster enzyme hydrolysate comprising the said peptide to a subject.

It is also an object of the present invention to provide a method for preventing cardiovascular disease containing the step of administering at least one of the said peptides to a subject.

It is also an object of the present invention to provide a use of the fraction of the oyster enzyme hydrolysate comprising the said peptide as a pharmaceutical composition for the prevention or treatment of cardiovascular disease.

It is also an object of the present invention to provide a use of at least one of the said peptides as a pharmaceutical composition for the prevention or treatment of cardiovascular disease.

It is also an object of the present invention to provide a use of the fraction of the oyster enzyme hydrolysate comprising the said peptide as a health food for the prevention or improvement of cardiovascular disease.

It is also an object of the present invention to provide a use of at least one of the said peptides as a health food for the prevention or improvement of cardiovascular disease.

To achieve the above objects, the present invention provides a peptide having angiotensin converting enzyme (ACE) inhibiting activity comprising one of the amino acid sequences represented by SEQ. ID. NO: 1~NO: 12.

The present invention also provides a pharmaceutical composition for the prevention and treatment of cardiovascular disease comprising the fraction of the oyster enzyme hydrolysate containing the said peptide as an active ingredient.

The present invention further provides a pharmaceutical composition for the prevention or treatment of cardiovascular disease comprising at least one of the said peptides as an active ingredient.

The present invention also provides a health food for the prevention or improvement of cardiovascular disease comprising the fraction of the oyster enzyme hydrolysate containing the said peptide as an active ingredient.

The present invention also provides a health food for the prevention or improvement of cardiovascular disease comprising at least one of the said peptides as an active ingredient.

The present invention also provides a method for treating cardiovascular disease containing the step of administering the fraction of the oyster enzyme hydrolysate comprising the said peptide to a subject having cardiovascular disease.

The present invention also provides a method for treating cardiovascular disease containing the step of administering at least one of the said peptides to a subject having cardiovascular disease.

The present invention also provide a method for preventing cardiovascular disease containing the step of administering the fraction of the oyster enzyme hydrolysate comprising the said peptide to a subject.

The present invention also provides a method for preventing cardiovascular disease containing the step of administering at least one of the said peptides.

The present invention also provides a use of the fraction of the oyster enzyme hydrolysate containing the said peptide as a pharmaceutical composition for the prevention or treatment of cardiovascular disease.

The present invention also provides a use of at least one of the said peptides as a pharmaceutical composition for the prevention or treatment of cardiovascular disease.

The present invention also provides a use of the fraction of the oyster enzyme hydrolysate containing the said peptide as a health food for the prevention or improvement of cardiovascular disease.

In addition, the present invention provides a use of at least one of the said peptides as a health food for the prevention or improvement of cardiovascular disease.

Advantageous Effect

The peptide of the present invention that shows angiotensin converting enzyme (ACE) inhibiting activity and has been separated from the fraction of the oyster enzyme hydrolysate has the effect of regulating blood pressure and of preventing hypertension thereby, so that the fraction of the oyster enzyme hydrolysate or the peptide isolated therefrom can be effectively used as an active ingredient for a pharmaceutical composition for the prevention or treatment of cardiovascular disease.

BRIEF DESCRIPTION OF THE DRAWINGS

The application of the preferred embodiments of the present invention is best understood with reference to the accompanying drawings, wherein:

FIG. 1 is a set of graphs illustrating the purification of the oyster enzyme hydrolysate. A indicates the purification by anion exchange chromatography, B indicates the purification by size exclusion chromatography of the fraction 4 obtained from the above anion exchange chromatography, and C indicates the purification by reverse-phase chromatography.

FIG. 2 is a set of graphs illustrating the mass and the amino acid sequence of the peptide separated from the oyster enzyme hydrolysate.

FIG. 3 is a graph illustrating the effect of in vivo blood pressure regulation by single administration of the oyster enzyme hydrolysate.

FIG. 4 is a graph illustrating the effect of in vivo blood pressure regulation by single administration of the functional peptide.

FIG. 5 is a graph illustrating the effect of in vivo blood pressure regulation by repeated administration of the oyster enzyme hydrolysate and the functional peptide.

FIG. 6 is a graph illustrating the inhibitory effect of the oyster enzyme hydrolysate and the functional peptide on the level of blood angiotensin converting enzyme (ACE).

FIG. 7 is a graph illustrating the inhibitory effect of the oyster enzyme hydrolysate and the functional peptide on the level of blood angiotensin-II.

FIG. 8 is a graph illustrating the preventive effect of the oyster enzyme hydrolysate and the functional peptide on hypertension in vivo.

DESCRIPTION OF THE PREFERRED EMBODIMENTS

Hereinafter, the present invention is described in detail.

The present invention provides a peptide having angiotensin converting enzyme (ACE) inhibiting activity comprising one of the amino acid sequences represented by SEQ. ID. NO: 1~NO: 12.

The peptide is preferably separated from the oyster enzyme hydrolysates, but not always limited thereto and the peptide can be originated from other natural sources or can be synthesized.

For the separation of the peptide, any conventional method such as ultrafiltration and chromatography which are well known to those in the art is preferred and chromatography is more preferred. Particularly, anion exchange chromatography, size exclusion chromatography, reverse-phase chromatography or high performance liquid chromatography (HPLC) is preferably used, but not always limited thereto.

For the synthesis of the peptide, the conventional peptide synthesis method such as chemical synthesis method is preferred (W. H. Freeman and Co., Proteins; structures and molecular principles, 1983). Particularly, solution phase peptide synthesis, solid-phase peptide syntheses, fragment condensation, F-moc, or T-BOC chemical method is more preferred, and among these methods, solid-phase peptide synthesis is most preferred, but not always limited thereto.

The enzyme herein is preferably the conventional protease that is well-informed to those in the art, and more preferably protamex or neutrase, but not always limited thereto. The addition of the enzyme is performed stepwise. Precisely, protamex is first reacted to induce inactivation and then neutrase is added, but not always limited thereto and protamex and neutrase can be added simultaneously. The preferable concentration of the enzyme is 0.1~10% by the concentration of the oyster enzyme hydrolysate protein. The inactivation of the enzyme is preferably induced at 20~100° C. for 10~120 minutes, but not always limited thereto and the inactivation condition can be modified by the kind of enzyme.

In a preferred embodiment of the present invention, the present inventors hydrolyzed the oyster protein by using a protease in order to prepare the oyster enzyme hydrolysate. Then, chromatography was performed to purify the functional peptide having ACE inhibiting activity from the oyster enzyme hydrolysate. As a result, 7 samples displaying ACE inhibiting activity were selected (see FIG. 1, Tables 1 and 2).

To screen the functional peptide having ACE inhibiting activity from the samples, mass and amino acid sequence of the peptide were confirmed. As a result, the peptide comprising one of the amino acid sequences represented by SEQ. ID. NO: 1~NO: 12 was selected (see FIG. 2 and Table 3). The peptide was chemically synthesized and then ACE inhibiting activity and cytotoxicity were investigated. As a result, all the peptides of the invention demonstrated ACE inhibiting activity without cytotoxicity (see Table 4).

Therefore, the peptide of the present invention can be effectively used as an ACE activity inhibitor since it demonstrates a significant ACE inhibiting activity without cytotoxicity.

The peptide of the present invention can be prepared by the below genetic engineering method. First, DNA sequence encoding the said peptide was constructed according to the conventional method. DNA sequence can be constructed by PCR using proper primers. DNA sequence can also be synthesized by other standard methods informed to those in the art such as the method using an automatic DNA synthesizer (for example, the product of Biosearch or Applied Biosystems). The DNA sequence was inserted in the vector containing one or more expression regulating sequences (for example, promoter, enhancer, etc.) that were operably linked to the said DNA sequence to express thereof, resulting in the construction of the recombinant expression vector. Host cells were transformed with the constructed recombinant expression vector and the generated transformant was cultured in a proper medium under the suggested condition to induce the expression of the DNA sequence. The pure peptide encoded by the DNA sequence was collected by the conventional method well known to those in the art (for example, chromatography). The "pure peptide" indicates the peptide that does not contain any other proteins originated from the host. The genetic engineering method used for synthesis of the peptide herein referred to: Maniatis et al., Molecular Cloning; A laboratory Manual, Cold Spring Harbor laboratory, 1982; Sambrook et al., Molecular Cloning: A Laboratory Manual, Cold Spring Harbor Press, N.Y., Second (1998) and Third (2000) Edition; Gene Expression Technology, Method in Enzymology, Genetics and Molecular Biology, Method in Enzymology, Guthrie & Fink (eds.), Academic Press, San Diego, Calif., 1991; and Hitzeman et al., J. Biol. Chem., 255:12073-12080, 1990.

The peptide of the present invention can be administered parenterally and be used in general forms of pharmaceutical formulation. The parenteral administration herein includes intrarectal, intravenous, intraperitoneal, intramuscular, intraarterial, percutaneous, intranasal, inhalation, ocular, and subcutaneous administration.

That is, the peptide of the present invention can be prepared for parenteral administration by mixing with generally used diluents or excipients such as fillers, extenders, binders, wetting agents, disintegrating agents and surfactants. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The peptide of the present invention can be mixed with many pharmaceutically acceptable carriers such as physiological saline or organic solvent, and can additionally include carbohydrates such as glucose, sucrose or dextran, antioxidants such as ascorbic acid or glutathion, chelating agents, low molecular proteins or other stabilizers to enhance stability or absorptiveness.

The effective dosage of the peptide of the present invention is 0.01~100 mg/kg per day, and preferably 0.1~10 mg/kg per day, and administration frequency is preferably 1~3 times a day.

The effective dose of the peptide of the present invention can be administered in the form of bolus, by single dose having relatively short period of infusion or by multiple dose of fractionated treatment protocol for a long term. The decision of an effective dosage of the peptide depends on the administration pathway, treatment times, age and other conditions of a patient, etc. Therefore, any expert who has knowledge on this field can decide the effective dosage of the peptide of the present invention.

The present invention also provides a pharmaceutical composition for the prevention and treatment of cardiovascular disease comprising the fraction of the oyster enzyme hydrolysate containing the peptide comprising one of the amino acid sequences represented by SEQ. ID. NO: 1~NO: 12 as an active ingredient.

The fraction herein is preferably up to 10 kD, but not always limited thereto.

The said cardiovascular disease is preferably one or more diseases selected from the group consisting of hypertension, heart disease, stroke, thrombosis, angina pectoris, heart failure, myocardial infarction, atherosclerosis, and arteriosclerosis, but not always limited thereto.

In another preferred embodiment of the present invention, the inventors administered the peptide to the hypertension mouse model via single or multiple administrations in order to investigate the blood pressure regulating activity of the peptide of the invention. As a result, the oyster enzyme hydrolysate and YA peptide were confirmed to have the significant antihypertensive activity (see FIGS. 4 and 5), and accordingly the levels of blood ACE and angiotensin-II were significantly decreased (see FIGS. 6 and 7).

To investigate the antihypertensive effect of the peptide of the invention in vivo, the present inventors administered the peptide of the invention to the mouse induced with hypertension, followed by examination of the antihypertensive effect. As a result, blood pressure in the mouse was significantly lowered (see FIG. 8).

Therefore, the fraction of the oyster enzyme hydrolysate containing the peptide comprising one of the amino acid sequence represented by SEQ. ID. NO: 1~NO: 12 had the blood pressure regulating activity and thereby antihypertensive effect, so that the fraction can be effectively used as an active ingredient of a pharmaceutical composition for the prevention or treatment of cardiovascular disease.

The composition of the present invention can be prepared for parenteral administration by mixing with generally used diluents or excipients such as fillers, extenders, binders, wetting agents, disintegrating agents and surfactants.

In addition to the ingredients mentioned above, the pharmaceutical composition of the present invention can include in a variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. The said carrier, excipient, or diluent can be selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, mineral oil, dextrine, calcium carbonate, propylene glycol, liquid paraffin, and saline, but not always limited thereto. All the mentioned ingredients can be added singly or together.

The pharmaceutical composition of the present invention can further be prepared in suitable forms according to ingredients by following the method represented in Remington's Pharmaceutical Science (the newest edition), Mack Publishing Company, Easton Pa.

The composition of the present invention is administered by the pharmaceutically effective dose. The term "pharmaceutically effective dose" herein indicates the amount enough to treat the disease with applicable, reasonable or risky concentration. The dose can be determined by considering many factors such as the type of disease, severity of the disease, activity of the drug, sensitivity to the drug, administration frequency and pathway, excretion, term of treatment, co-treatment drug and other factors regarded as relevant in the medicinal field. The composition of the present invention can be administered as an individual drug or co-administered with other agents together, and at this time it can be administered serially or simultaneously with the other agents. Single or multiple application is also accepted. It is important to determine the dose to bring the maximum effect with the minimum amount without side effects, which can be easily determined by those in the art.

The effective dose of the pharmaceutical composition of the present invention can be determined according to weight, age, gender, health condition, diet, administration frequency, administration method, excretion and severity of a disease. The preferable effective dose of the composition is 0.01~1000 mg/kg per day, preferably 30~500 mg/kg per day, and more preferably 50~300 mg/kg per day, and administration times are 1~6 per day. However, the dose can be adjusted by considering various factors such as administration pathway, severity of disease, patient's age, gender and weight, etc. Therefore, the preferable dose cannot limit the scope of the invention in any way.

The composition of the present can be administered alone or treated together with surgical operation, radio-therapy, hormone therapy, chemo-therapy and biological regulators.

The present invention also provides a pharmaceutical composition for the prevention or treatment of cardiovascular disease comprising one or more peptides composed of the amino acid sequences represented by SEQ. ID. NO: 1~NO: 12 as an active ingredient.

The peptide of the present invention displays effective blood pressure regulating activity and antihypertensive effect thereby, so that any of those peptides of the invention can be effectively used as an active ingredient of a pharmaceutical composition for the prevention or treatment of cardiovascular disease.

The present invention also provides a health food for the prevention or improvement of cardiovascular disease comprising the fraction of the oyster enzyme hydrate containing the said peptide comprising one of the amino acid sequences represented by SEQ. ID. NO: 1~NO: 12 as an active ingredient.

The present invention also provides a health food for the prevention or improvement of cardiovascular disease comprising at least one of the said peptides as an active ingredient.

The fraction of the oyster enzyme hydrolysate of the present invention or the peptide isolated therefrom displays excellent ACE inhibiting activity, suggesting that it could have efficient blood pressure regulating activity and antihypertensive effect thereby. Therefore, the fraction of the oyster enzyme hydrolysate and the peptide separated from the same can be effectively used as an active ingredient of a health food for the prevention or improvement of cardiovascular disease.

The food herein is not limited. For example, the peptide of the present invention can be added to drinks, meats, sausages, breads, biscuits, rice cakes, chocolates, candies, snacks, cookies, pizza, ramyuns, gums, dairy products including ice cream, special nutritious food such as milk formulas or young children diet, processed meat products, fish products, Tofu, starch gel products, health supplement food, seasoning food such as soy sauce, soybean paste, red pepper paste or mixed sauce, sauces, other processed food, pickles such as Kimchi or Jangajji, soups, beverages, alcohol drinks and vitamin complex, and in wide sense, almost every food applicable in the production of health food can be included.

The "health food" in this invention indicates the value added food group that is designed to be functioning for a specific purpose or to induce a full expression of its composition via physical, biochemical, or biotechnological technique, or the processed food designed to induce a full expression of each component of the food to regulate bio defense system or other regulation system involved in disease prevention and recovery. More preferably, the health food of the invention indicates the food that can induce the full action of body regulating functions involved in the prevention or improvement of cardiovascular disease. The said health food can contain additives that can be accepted in the food industry and generally used carriers, excipients, and diluents in the preparation of health food.

The fraction of the oyster enzyme hydrolysate of the present invention or the peptide isolated therefrom can be used as food additive. In that case, the fraction of the oyster enzyme hydrolysate of the present invention or the peptide isolated therefrom can be added as it is or as mixed with other food components according to the conventional method. The mixing ratio of active ingredients can be regulated according to the purpose of use (prevention or health enhancement). In general, to produce health food or beverages, the fraction of the oyster enzyme hydrolysate of the present invention or the peptide isolated therefrom is added preferably by 0.1~90 weight part. However, if long term administration is required for health and hygiene or regulating health condition, the content can be lower than the above but higher content can be accepted as well since the fraction of the oyster enzyme hydrolysate of the present invention or the peptide isolated therefrom has been proved to be very safe.

The composition for health beverages of the present invention can additionally include various flavors or natural carbohydrates, etc, like other beverages, in addition to the extract of crude drug complex. The natural carbohydrates above can be one of monosaccharides such as glucose and fructose, disaccharides such as maltose and sucrose, polysaccharides such as dextrin and cyclodextrin, and sugar alcohols such as xilytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1~20 g and more preferably 5~12 g in 100 ml of the composition.

In addition to the ingredients mentioned above, the fraction of the oyster enzyme hydrolysate of the present invention or the peptide isolated therefrom can include in a variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The fraction of the oyster enzyme hydrolysate of the present invention or the peptide isolated therefrom can also include natural fruit juice, fruit beverages and/or fruit flesh addable to vegetable beverages. All the mentioned ingredients can be added singly or together. The mixing ratio of those ingredients does not matter in fact, but in general, each can be added by 0.1~20 weight part per 100 weight part of the fraction of the oyster enzyme hydrolysate of the present invention or the peptide isolated therefrom.

The present invention also provides a method for treating cardiovascular disease containing the step of administering the fraction of the oyster enzyme hydrolysate containing the said peptide comprising one of the amino acid sequences represented by SEQ. ID. NO: 1~NO: 12 to a subject having cardiovascular disease.

The present invention also provides a method for treating cardiovascular disease containing the step of administering at least one of the said peptides to a subject having cardiovascular disease.

The fraction of the oyster enzyme hydrolysate of the present invention or the peptide isolated therefrom displays excellent ACE inhibiting activity, suggesting that it could have efficient blood pressure regulating activity and antihypertensive effect thereby. Therefore, the fraction of the oyster enzyme hydrolysate and the peptide separated from the same can be effectively used for the method for treating cardiovascular disease.

The present invention also provide a method for preventing cardiovascular disease containing the step of administering the fraction of the oyster enzyme hydrolysate containing the said peptide comprising one of the amino acid sequences represented by SEQ. ID. NO: 1~NO: 12 to a subject.

The present invention also provides a method for preventing cardiovascular disease containing the step of administering at least one of the said peptides.

The fraction of the oyster enzyme hydrolysate of the present invention or the peptide isolated therefrom displays excellent ACE inhibiting activity, suggesting that it could have efficient blood pressure regulating activity and antihypertensive effect thereby. Therefore, the fraction of the oyster enzyme hydrolysate and the peptide separated from the same can be effectively used for the method for preventing cardiovascular disease.

The present invention also provides a use of the fraction of the oyster enzyme hydrolysate containing the said peptide comprising one of the amino acid sequences represented by SEQ. ID. NO: 1~NO: 12 as a pharmaceutical composition for the prevention or treatment of cardiovascular disease.

The present invention also provides a use of at least one of the said peptides as a pharmaceutical composition for the prevention or treatment of cardiovascular disease.

The present invention also provides a use of the fraction of the oyster enzyme hydrolysate containing the said peptide as a health food for the prevention or improvement of cardiovascular disease.

In addition, the present invention provides a use of at least one of the said peptides as a health food for the prevention or improvement of cardiovascular disease.

The fraction of the oyster enzyme hydrolysate of the present invention or the peptide isolated therefrom displays excellent ACE inhibiting activity, suggesting that it could have efficient blood pressure regulating activity and antihypertensive effect thereby. Therefore, the fraction of the oyster enzyme hydrolysate and the peptide separated from the same can be effectively used as an active ingredient of a pharmaceutical composition for the prevention or treatment of cardiovascular disease or a health food for the prevention or improvement of cardiovascular disease.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Preparation of Oyster Enzyme Hydrolysate

To prepare the oyster enzyme hydrolysate of the present invention, oyster protein was hydrolyzed by using an enzyme.

Particularly, 3 kg of the cultured oyster (purchased from the Oyster Hanging Fisheries Cooperatives, Tongyeong-si, Gyeongsangnam-do, Korea) was parboiled for 3 minutes and then water was drained by a strainer. Water was added to the oyster twice the volume of the oyster, followed by grinding with a grinder (M-12S, Hankook Fujee Machinery Co., Ltd., Korea) at 3000 rpm for 2 minutes. The grinded oyster and transglutaminase (TGase; Ajinomoto Co., Inc., Japan) were loaded in 5 L Jar fermenter (Korea Fermenter, Korea), followed by reaction at 30° C. for 1 hour with stirring at 150 rpm. The reaction mixture was inactivated by heating at 100° C. for 1 hour. Protamex (Nobozymes-Korea), the *Bacillus* originated protease was added thereto, followed by reaction at 40° C. for 1 hour. As a result, the primary oyster enzyme hydrolysate was obtained. The primary oyster enzyme hydrolysate was treated at 100° C. for 1 hour to make Protamex inactivated. Then, Neutrase (Nobozymes-Korea) was added thereto, followed by reaction at 50° C. for 1 hour. As a result, the secondary oyster enzyme hydrolysate was obtained. The secondary oyster enzyme hydrolysate was treated at 100° C. for 1 hour to make Neutrase inactivated. Then, the secondary oyster enzyme hydrolysate was centrifuged to obtain supernatant. Ethanol was added to the supernatant at the volume of 60% (v/v) at 4° C., followed by reaction for 1 hour to induce the precipitation of ethanol-insoluble materials and the remaining proteins. Centrifugation was performed at 8000×g for 25 minutes to obtain supernatant. The obtained supernatant was filtered with 0.45 μm membrane filter and ethanol was evaporated by using a rotary vacuum evaporator (N-1 type, EYELA, Japan) at 40° C. The resultant oyster enzyme hydrolysate was freeze-dried or spray-dried and stored.

Example 2: Purification of Functional Peptide Having Angiotensin-I Converting Enzyme (ACE) Inhibiting Activity <2-1> Purification by Anion Exchange Chromatography To purify the functional peptide having ACE inhibiting activity from the oyster enzyme hydrolysate, anion exchange chromatography was performed.

Particularly, 0.5 g of the oyster enzyme hydrolysate prepared in Example <1-1> was dissolved in 12 ml of 20 mM Tris-HCl buffer (pH 7.5), which was loaded in Q-Sepharose column (16×100 mm; GE Healthcare-Korea), followed by anion exchange chromatography under the conditions shown in Table 1. Then the oyster enzyme hydrolysate fractions were obtained, 2 ml each, and the detected peptides were confirmed.

As a result, as shown in FIG. 1, the fractions containing the peptide separated from the oyster enzyme hydrolysates were obtained (FIG. 1).

TABLE 1

Chromatography condition for functional peptide purification

| Chromatography | Column | Solvent | Flow rate (ml/min) | Detection wavelength (nm) |
|---|---|---|---|---|
| Anion exchange chromatography | Q-Sepharose column (16 × 100 mm) | A*: 20 mM Tris-HCl buffer (pH 7.5) B: containing 0.75M NaCl 20 mM Tris-HCl buffer (pH 7.5) | 1 | 254 |
| Size exclusion chromatography $^a$ | Superdex peptide (10 × 300 mm) | 20 mM Tris-HCl buffer (pH 7.5) | 0.5 | 216 and 254 |
| Reverse-phase chromatography $^b$ | Source 5RPC ST (4.6 × 150 mm) | A**: 0.1% TFA$^c$ solution B: 0.09% TFA and 60% ACN$^d$ solution | 1 | 216 and 254 |

$^a$ size exclusion chromatography
$^b$ reverse-phase chromatography
$^c$TFA: trifluoroacetic acid
$^d$ACN: acetonitrile
*solvent density gradient: 100 ml/100 min., 0~100% solvent B density gradient.
**solvent density gradient: 90 ml/90 min., linear gradation.

<2-2> Confirmation of ACE Inhibiting Activity

To investigate ACE inhibiting activity of the fraction obtained in Example <2-1>, ACE activity was measured by using the method of Wu et al (Wu et al., 2002; J Chromatography A 950:125-130) with slight modifications.

Particularly, 0.1 M borate buffer (pH 8.3) containing 0.3 M NaCl, 5 mM N-benzoyl-Gly-His-Leu (HHL; Sigma; product # H1635), and 0.25 mUnit ACE (Sigma, USA) was prepared as the reaction solution. Then, 40 μl of the fraction prepared in Example <2-1> was mixed with 150 μl of the reaction solution above, followed by reaction with stirring in a 37° C. water bath for 30 minutes. Upon completion of the reaction, 150 μl of 1 M HCl was added to terminate ACE reaction, followed by centrifugation at 10,000 rpm for 10 minutes to obtain supernatant using a centrifuge (product name: 5415C; Eppendorf, Hamburg, Germany). 20 μl of the obtained supernatant was loaded on high performance liquid chromatography (HPLC) equipped with reverse-phase column (Watchers 120 ODS-AP, 4.6×250 mm, 5 μm; Daiso, Japan), from which the content of hippuric acid (HA) dissociated from HHL by ACE was measured. For HPLC, 0.1% TFA aqueous solution was used as solvent A and acetonitrile containing 0.1% TFA was used as solvent B for the linear gradation under the conditions of 5~60% solvent B/20 minutes. During the elution at 1 ml/min, $OD_{228}$ was measured. Then, ACE inhibiting activity was calculated by the below mathematical formula 1. Dose-dependent ACE inhibiting activity was analyzed by linear regression analysis (JMP statistics package ver. 7, SAS Institute, Cary, N.C., USA) and then $IC_{50}$, the concentration of the sample that was able to inhibit ACE activity by 50%, was calculated to investigate ACE inhibiting activity. For the negative control, 20 μl of 0.1% TFA aqueous solution was used instead of the sample. Then, ACE inhibiting activity was measured by the same manner as described above.

ACE inhibiting activity (%)=HA$o$−
    HA/HA$o$×100    [Mathematical Formula 1]

HAo: HA conc. of negative control

HA: HA conc. of sample

As a result, as shown in Table 2, ACE inhibiting activity was observed in the samples of fractions 2, 3, and 4.

<2-3> Purification by Size Exclusion Chromatography

To purify the functional peptide having ACE inhibiting activity from the oyster enzyme hydrolysate, size exclusion chromatography was performed.

Particularly, the fractions 2, 3, and 4 selected in Example <2-2> were concentrated in Speed Vacuum Concentrator (scan speed 40, Labgene Aps, Denmark). 200 μl of the concentrated sample was loaded on superdex peptide column (10×300 mm; GE Healthcare-Korea), followed by size exclusion chromatography over the molecular weight under the conditions shown in Table 1. The fraction of each sample was investigated by the same manner as described in Example <2-2> to confirm ACE inhibiting activity.

As a result, as shown in FIG. 1 and Table 2, the fractions 2-1, 2-2, 2-3, 3-1, 3-2, 4-1, and 4-2 containing the said peptide were selected through size exclusion chromatography (FIG. 1). These fractions were confirmed to have ACE inhibiting activity (Table 2).

<2-4> Purification by Reverse-Phase Chromatography

To purify the functional peptide having ACE inhibiting activity from the oyster enzyme hydrolysate, reverse-phase HPLC was performed.

Particularly, the fractions 2-1, 2-2, 2-3, 3-1, 3-2, 4-1, and 4-2 selected in Example <2-3> were loaded in source 5 RPC ST column (4.6×150 mm; GE Healthcare-Korea), followed by reverse-phase chromatography over the molecular weight under the conditions shown in Table 1. The fraction of each sample was investigated by the same manner as described in Example <2-2> to confirm ACE inhibiting activity.

As a result, as shown in FIG. 1 and Table 2, the fractions containing the said peptide were selected through reverse-phase chromatography (FIG. 1). These fractions were confirmed to have ACE inhibiting activity (Table 2).

TABLE 2

Fraction name, fraction number, ACE inhibiting activity and peptide sequence according to purification stage

| Purification | Fraction name | Fraction number | ACE inhibiting activity (%) | Peptide |
|---|---|---|---|---|
| Anion exchange chromatography | 2 | 25, 26, 27 | 4.0 | |
| | 3 | 29 | 4.9 | |
| | 4 | 30, 31 | 6.7 | |
| Size exclusion chromatography | 2-1 | 19, 20 | 19.0 | |
| | 2-2 | 21 | 17.0 | |
| | 2-3 | 23 | 15.0 | |
| | 3-1 | 20 | 15.7 | |
| | 3-2 | 21 | 17.8 | |
| | 4-1 | 20, | 18.3 | |
| | 4-2 | 21, 22 | 18.6 | |
| Reverse-phase chromatography | 2-1-3 | 20, 21 | 34.0 | AFN, FYN |
| | 2-2-2 | 21, 21 | 27.7 | TAY |
| | 2-3-2 | 16, 17 | 30.4 | KY |
| | 3-1-4 | 20, 21 | 54.5 | AFY |
| | 3-2-2 | 14 | 44.3 | VK |
| | 4-1-1 | 18, 19 | 34.4 | PGN, GPN |
| | 4-2-1 | 16 | 26.5 | MC, PH, SF, YA |

Example 3: Investigation of Mass and Sequence of the Functional Peptide Having ACE Inhibiting Activity To screen the functional peptide having ACE inhibiting activity separated from the oyster enzyme hydrolysate, the mass and the amino acid sequence of the said peptide were investigated by Edman degradation and MALDI/TOF (Matrix-Assisted Laser Desorption Ionization/Time-Of-Flight Mass Spectroscopy).

Particularly, 7 samples displaying ACE inhibiting activity selected in Example <2-4> were completely dried in a vacuum centrifugal concentrator, to which 20 μl of 0.1% TFA aqueous solution was added until the samples were fully dissolved. Then, 50% acetonitrile was added to induce activation and the dissolved samples were loaded in ZipTip C18 column (Fierce, product #: 87782) equilibrated with 0.1% TFA aqueous solution. Then, the column was washed with 0.1% TFA aqueous solution 2~3 times. The peptide was eluted by using 70% acetonitrile containing 0.1% TFA to eliminate the remaining salts. 10 μl of the eluted peptide solution was loaded on biobrene (AB Systems, USA) pretreated micro-filter, and the filter was dried over argon gas. When the filter was dried, it was loaded in the cartridge and the amino acid sequence that composed the functional peptide was analyzed by pulsed-liquid method using ABI482 automated protein sequencer (Applied Biosystems, USA).

The 7 samples displaying ACE inhibiting activity selected in Example <2-4> proceeded to the mass spectrometer Q-TOF2 (Micromass, United Kingdom) based on electrospray Ionization (ESI) to perform data dependent MS/MS via Nano-ESI-interface.

As a result, as shown in FIG. 2 and Table 3, total 12 peptides composed of the amino acid sequences represented by SEQ. ID. NO: 1~NO: 12 were confirmed (Table 3 and FIG. 2).

TABLE 3

Amino acid sequences of the functional peptides showing ACE inhibiting activity

| Peptide | Sample | Amino acid sequence |
|---|---|---|
| TAY (SEQ. ID. NO: 1) | 1-2-2 | threonine-alanine-tyrosine |
| VK (SEQ. ID. NO: 2) | 2-2-2 | valine-lysine |
| KY (SEQ. ID. NO: 3) | 1-3-2 | lysine-tyrosine |
| YA (SEQ. ID. NO: 4) | 3-2-1 | tyrosine-alanine |
| FYN (SEQ. ID. NO: 5) | 1-1-3 | phenylalanine-tyrosine-asparagine |
| AFY (SEQ. ID. NO: 6) | 2-1-4 | alanine-phenylalanine-tyrosine |
| MC (SEQ. ID. NO: 7) | 3-2-1 | methionine-cysteine |
| GPN (SEQ. ID. NO: 8) | 3-1-1 | glycine-proline-asparagine |
| AFN (SEQ. ID. NO: 9) | 1-1-3 | alanine-phenylalanine-asparagine |
| PGN (SEQ. ID. NO: 10) | 3-1-1 | proline-glycine-asparagine |
| PH (SEQ. ID. NO: 11) | 3-2-1 | proline-histidine |
| SF (SEQ. ID. NO: 12) | 3-2-1 | serine-phenylalanine |

Example 4: Synthesis of the Functional Peptide Showing ACE Inhibiting Activity and Confirmation of the Activity <4-1> Synthesis of the Functional Peptide To investigate whether or not the functional peptide separated from the oyster enzyme hydrolysate could have ACE inhibiting activity, Fmoc-SPPS (Fluorenylmethyloxycarbonyl chloride-Solid phase peptide synthesis) was performed to prepare synthetic peptides.

Particularly, the amino acid in which C-terminal was binding to resin, N-terminal was protected by Fmoc, and also the residue was protected by such protection group as trityl (Trt), t-butyloxycarbonyl (Boc), or t-butyl (t-Bu) was prepared as the material for the amino acid synthesis that composed the peptide sequence confirmed in Example 3. The prepared amino acid was added to coupling reagent containing 2-(1H-Benzotirazloe-1-yl)-1,1,3,3-tetramethyluronium hexafluorophosphate (HBTU), hydroxybenzotriazole (HOBt) and N-methylmorpholine (NMM), followed by reaction using an automatic synthesizer (ASP48S; Peptron, Korea) at room temperature for 2 hours. Dimethylformamide (DMF) containing 20% piperidine was added thereto, followed by reaction at room temperature for 5 minutes, during which Fmoc was eliminated, resulting in the synthesis of the peptide. The peptide of the present invention was synthesized by repeating the process. Next, TFA, 1,2-ethanedithiol (EDT), Thioanisole, Triisopropylsilane (TIS), and water were mixed at the ratio of 90%, 2.5%, 2.5%, 2.5%, and 2.5% (v/v), to which the synthesized peptide was added. The resin conjugated at C-terminal and the protection group in the residue were eliminated. Reverse-phase HPLC was performed using Vydac Everest C18 column (22×250 mm, 10 μm; Grace, USA) under the linear gradation condition with 40% acetonitrile solution containing 0.1% TFA, resulting in the separation and purification of the peptide. The purified peptide was confirmed by LC/MS using Agilent HP1100 series (Agilent, USA).

As a result, 12 synthetic peptides composed of the same amino acid sequences as those composing the functional peptides separated from the oyster enzyme hydrolysates were prepared.

<4-2> Confirmation of ACE Inhibiting Activity and Cytotoxicity of the Synthetic Peptide To investigate if the functional peptide separated from the oyster enzyme hydrolysate could have ACE inhibiting activity, the synthetic peptide was tested and MTT assay was performed to confirm the cytotoxicity.

Particularly, ACE inhibiting activity of the peptide synthesized in Example <4-1> was investigated by the same manner as described in Example <2-2>. To measure the cytotoxicity, the liver cancer cell line HepG2 was inoculated in MEM supplemented with antibiotics and 10% fetal bovine serum (FBS), followed by culture at 37° C. with 5% $CO_2$. When the cells were grown to 80% confluency, the cells were washed with phosphate-buffered saline-ethylenediaminetetraacetic acid (PBS-EDTA) and then treated with trypsin, followed by sub-culture. The medium was replaced every 48 hours during the cell culture. The cells were distributed in a 96-well plate at the density of $1 \times 10^5$ cells/ml, 100 μl/well, followed by culture for 24 hours to attach the cells onto the plate. Then, the medium was discarded. The peptide synthesized in Example <4-1> was dissolved in MEM containing 0.2% PBS at the concentrations of 10 μg/ml, 50 μg/ml, 100 μg/ml, or 200 μg/ml. The peptide was treated to the cells above, followed by further culture for 24 hours. Upon completion of the culture, the cells were washed with PBS twice, and then treated with MTT reagent. The cells were further cultured for 2 hours and $OD_{490}$ was measured with ELISA plate reader.

As a result, as shown in Table 4, it was confirmed that all of those 12 functional peptides did not show cytotoxicity but had ACE inhibiting activity (Table 4).

TABLE 4

ACE inhibiting activity and cytotoxicity of functional peptide

| Peptide | ACE inhibiting activity | | Cytotoxicity (%) |
|---|---|---|---|
| | $IC_{50}$ (μM) | $IC_{50}$ (μg/μl) | |
| TAY | 16.7 | 2.18 | 101.2 ± 6.1 |
| VK | 29.0 | 2.63 | 103.2 ± 3.9 |
| KY | 51.5 | 5.90 | 105.4 ± 5.7 |
| YA | 93.9 | 8.76 | 103.8 ± 7.7 |
| FYN | 68.2 | 11.17 | 109.5 ± 3.0 |
| AFY | 75.6 | 11.18 | 106.7 ± 7.4 |
| MC | 153.8 | 14.36 | 100.6 ± 4.6 |
| GPN | 208.5 | 22.09 | 108.3 ± 1.0 |
| AFN | 222.9 | 28.89 | 108.1 ± 4.4 |
| PGN | 371.9 | 39.39 | 103.9 ± 6.2 |
| PH | 537.1 | 50.13 | 113.7 ± 6.0 |
| SF | 646.3 | 60.33 | 99.0 ± 1.2 |

Example 5: In Vivo Blood Pressure Regulation by the Oyster Enzyme Hydrolysate and the Functional Peptide Separated Therefrom <5-1> Separation of the Oyster Enzyme Hydrolysate According to the Molecular Weight To investigate in vivo blood pressure regulation effect of the oyster enzyme hydrolysate according to the molecular weight, the oyster enzyme hydrolysate was divided into two groups; one with the molecular weight of at least 10 kD and the other with the molecular weight of under 10 kD.

Particularly, the oyster enzyme hydrolysate prepared in Example 1 was filtered by ultrafiltration (Labscale TFF system, Millipore, USA) using Biomax 10 ultrafiltration membrane (Millipore, USA) and pellicon XL ultrafiltration membrane (Millipore, USA).

As a result, the oyster enzyme hydrolysate having either 10 kD or higher molecular weight or 10 kD or lower molecular weight was obtained from the whole oyster enzyme hydrolysate.

<5-2> Investigation of In Vivo Blood Pressure Regulation Effect by a Single Administration To investigate in vivo blood pressure regulation effect of the functional peptide separated from the oyster enzyme hydrolysate by a single administration, the peptide was administered to the hypertension animal model once (single administration), followed by the investigation of blood pressure.

Particularly, male spontaneously hypertensive rats (SHR; Central Lab. Animal Inc.) at 11 weeks and Wistar rats (Central Lab. Animal Inc.) were purchased, which were raised in a laboratory animal room in which the temperature was regulated at 22±3° C., the humidity was controlled at 50±5%, and the light/dark cycle was set at 12 h/12 h. Feeds and drinking water were provided freely. After a week of adaptation, the animals were divided into the experimental and the control groups and used for the experiment according to the guide line of Association for Assessment and Accreditation of Laboratory Care International approved by Institutional Animal Care and Use Committee, Kyunghee University College of Pharmacy. The experimental and the control groups were divided by the conditions shown in Table 5. The animals were orally or intraperitoneally administered with the oyster enzyme hydrolysate prepared in Example 1, the oyster enzyme hydrolysate having the molecular weight of at least 10 kD or up to 10 kD prepared in Example <5-1>, the peptide prepared in Example <4-1>, or Captopril (Boryung Co., Ltd., Korea). Then the animals were fixed for 20 minutes in a rat temperature control unit in which the temperature was maintained at 42° C. at the time point of 0, 3, 6, 9, 12, and 24 h, to let the tail vessel fully expanded. Then, systolic pressure was measured to investigate the antihypertensive activity.

As a result, as shown in FIG. 3 and FIG. 4, in the positive control treated with Captopril, the conventional antihypertensive agent, the blood pressure lowering effect was only 18~19% by that of the negative control hypertensive rat model. In the meantime, when the oyster enzyme hydrolysate was administered, the blood pressure lowering effect was increased to 33~38% by the negative control. In particular, when the oyster enzyme hydrolysate having the molecular weight of up to 10 kDa, blood pressure of the experimental group was significantly lowered almost back to that of the normal control until 12 hours from the administration of the oyster enzyme hydrolysate (FIG. 3).

In the experimental group treated with the functional peptide of the invention, a significant blood pressure lowering effect was observed, compared with that of the negative control hypertensive model. In particular, when peptide YA was administered, the blood pressure lowering effect after 6 hours from the administration was 33.9%, which was the highest effect of all (FIG. 4).

<5-3> Investigation of In Vivo Blood Pressure Regulation Effect by the Repeated Administration To investigate in vivo blood pressure regulation effect of the functional peptide separated from the oyster enzyme hydrolysate by the repeated administration, the peptide was administered to the hypertension animal model repeatedly, followed by the investigation of blood pressure.

Particularly, the same rats as described in Example <5-2> were purchased and raised under the same condition. The rats were divided into the experimental and the control groups according to the conditions as shown in Table 6, to which the oyster enzyme hydrolysate having the molecular weight of up to 10 kD prepared in Example <5-1>, the peptide YA prepared in Example <4-1>, or Val-Tyr, the antihypertensive material separated from sardine hydrolysate were administered orally, every morning at 10 am, for 4 weeks. Systolic pressure was measured by the same manner as described in Example <5-2> on week 0, week 1, week 2, week 3, and week 4. 4 weeks after the administration began, the rats were sacrificed and blood was extracted from the inferior vena cava. The blood sample was centrifuged at 3,000 rpm for 10 minutes, and as a result serum was obtained and stored at −80° C. The levels of blood ACE and angiotensin-II in the stored serum were measured by using a commercial ELISA kit (USCN Life Science, China) according to the manufacturer's protocol.

TABLE 5

Conditions for the experimental and the control groups to confirm the in vivo blood pressure regulation effect by a single administration

| Animal | | | Administration dose$^a$ |
|---|---|---|---|
| Wistar Rat | Normal control | Saline | 2 ml |
| SHR | Negative control | Saline | 2 ml |
| | Positive control | Captopril | 8 mg/kg |
| | Experimental group | Oyster enzyme hydrate | Whole Over 10 kD Less 10 kD | 100 mg/kg |
| | | Functional peptide | TAY VK KY YA FYN AFY MC | 50 μg/kg |

$^a$The dose of the sample presented as mg/kg for the positive control and the experimental groups was mixed with 2 ml of saline for the administration.

TABLE 6

Conditions for the experimental and the control groups to confirm the in vivo blood pressure regulation effect by the repeated administration

| Animal | | | Administration dose$^a$ |
|---|---|---|---|
| Wistar Rat | Normal control | Saline | 2 ml |
| SHR | Negative control | Saline | 2 ml |
| | Positive control | Val-Tyr | 50 μg/kg |
| | Experimental group | Oyster enzyme hydrate | Whole Less than 10 kD | 100 mg/kg |
| | | Functional peptide | YA | 50 μg/kg |

$^a$The dose of the sample presented as mg/kg for the positive control and the experimental groups was mixed with 2 ml of saline for the administration.

As a result, as shown in FIGS. 5~7, a significant blood pressure lowering effect was observed in all the experimental groups, compared with the negative control hypertensive rat model. Particularly, in the groups treated with peptide YA and the whole oyster enzyme hydrolysate, blood pressure did not increase for 2 weeks from the administration. In the group treated with the oyster enzyme hydrolysate of up to 10 kD, blood pressure was slightly increased for 2 weeks from the administration, but from the third week the blood pressure lowering effect began to display, which was significantly increased further on (FIG. 5).

The level of blood ACE was reduced in all the experimental groups, compared with that of the negative control hypertensive group (FIG. 6). The level of blood angiotensin-II was also significantly reduced in all the experimental groups, compared with that of the negative control group, which was more significant than that of the positive control administered with Val-Tyr, the antihypertensive functional peptide separated from sardine hydrolysate. Particularly, in the group treated with the oyster enzyme hydrolysate of up to 10 kD, the level of blood angiotensin-II was almost same as that of the normal control group (FIG. 7).

Example 6: Hypertension Preventive Effect of the Oyster Enzyme Hydrolysate and the Functional Peptide Separated from the Same To investigate the hypertension preventive effect of the functional peptide separated from the oyster enzyme hydrolysate, the peptide was administered to the hypertension animal model, and then the antihypertensive effect was observed.

Particularly, male Wistar rats at 12~16 weeks were purchased and raised in a laboratory animal room in which the temperature was regulated at 22±3° C., the humidity was controlled at 50±5%, and the light/dark cycle was set at 12 h/12 h. Feeds and drinking water were provided freely. After a week of adaptation, the rats were divided into the experimental and the control groups (8 rats/group) according to the conditions listed in Table 7. To induce hypertension, the rats of the experimental and control groups were administered with nitro-L-arginine methyl ester (L-NAMA; Fluka) at the concentration of 40 mg/kg via intravenous injection every day. Then, the rats were orally administered with the oyster enzyme hydrolysate prepared in Example 1, the oyster enzyme hydrolysate of up to 10 kD prepared in Example <5-1>, the peptide YA prepared in Example <4-2>, Captopril, or Val-Tyr. Systolic pressure was measured by the same manner as described in Example <5-2> on week 0, week 1, week 2, week 3, and week 4. Then average systolic pressure of each control and experimental group was calculated.

TABLE 7

Conditions for the experimental and the control groups to confirm the in vivo hypertension preventive effect of the oyster enzyme hydrate and the functional peptide separated therefrom

| Animal | | | Administration dose[a] |
|---|---|---|---|
| Wistar Rat | Normal control | Saline | 2 ml |
| | Negative control | Saline | 2 ml |
| | Positive control | Captopril | 8 mg/kg |
| | | Sardine peptide | 100 mg/kg |
| | | Val-Tyr | 50 μg/kg |
| | Experimental group | Oyster enzyme hydrate | Whole | 100 mg/kg |
| | | | Less than 10 kD | 100 mg/kg |
| | Functional peptide | YA | 50 μg/kg |

[a]The dose of the sample presented as mg/kg for the positive control and the experimental groups was mixed with 2 ml of saline for the administration.

As a result, as shown in FIG. 8, normal rats were induced with hypertension by treating L-NAMA. Compared with the positive control group, the blood pressure increase was significantly suppressed in the rat group administered with the oyster enzyme hydrolysate and the functional peptide (FIG. 8).

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treating cardiovascular disease comprising the step of administering a fraction of an oyster enzyme hydrolysate containing at least one peptide consisting of the amino acid sequence selected from the group consisting of SEQ ID NOs: 1, 2 and SEQ ID NOs. 5-11 to a subject having cardiovascular disease.

2. The method according to claim 1, wherein the fraction of the oyster enzyme hydrolysate has a molecular weight up to 10 kD.

3. The method according to claim 1, wherein the cardiovascular disease is one or more diseases selected from the group consisting of hypertension, heart disease, stroke, thrombosis, angina pectoris, heart failure, myocardial infarction, atherosclerosis, and arteriosclerosis.

* * * * *